United States Patent [19]

DeLuca et al.

[11] 4,223,131
[45] Sep. 16, 1980

[54] 25-HYDROXYCHOLECALCIFEROL-26,23-LACTONE

[75] Inventors: Hector F. DeLuca; Heinrich K. Schnoes; Joseph K. Wichmann, all of Madison, Wis.

[73] Assignee: Wisconsin Alumni Research Foundation, Madison, Wis.

[21] Appl. No.: 7,473

[22] Filed: Jan. 26, 1979

[51] Int. Cl.$^2$ ............................................. C07D 307/32
[52] U.S. Cl. ..................................... 542/428; 424/279
[58] Field of Search ........................................... 542/428

Primary Examiner—Norma S. Milestone
Attorney, Agent, or Firm—Howard W. Bremer

[57] ABSTRACT

The invention provides a new derivative of vitamin D, 25-hydroxycholecalciferol-26,23-lactone.

The compound is characterized by vitamin D-like activity in its ability to increase serum calcium concentration by mobilizing bone and would find application in disease states requiring the elevation of serum calcium concentration.

1 Claim, No Drawings

25-HYDROXYCHOLECALCIFEROL-26,23-LACTONE

The invention described herein was made in the course of work under a grant or award from the Department of Health, Education, and Welfare.

DESCRIPTION

1. Technical Field

This invention relates to a compound which is characterized by vitamin D-like activity.

More specifically this invention relates to a derivative of vitamin D.

Still more specifically this invention relates to 25-hydroxycholecalciferol-26,23-lactone.

The ability of the D vitamins to raise serum calcium concentrations and to enhance the growth of bone is well known and the use of these vitamins as nutritional supplements is well established.

It is also well known that to be effective these vitamins must be metabolized in vivo to express the physiological functions with which they are associated. The vitamin is first hydroxylated in the liver to form 25-hydroxyvitamin D, considered to be the major circulating metabolite in the blood stream. This compound is then further hydroxylated in the kidney to produce 1α,25-dihydroxyvitamin D or 24,25-dihydroxyvitamin D. The 1α-hydroxylated form of vitamin D is generally considered to be the physiologically active or hormonal form of the vitamin, and to be responsive for what are termed vitamin D-like activities, such as increasing intestinal absorption of calcium and phosphate, mobilizing bone mineral, and retaining calcium in the kidneys. The possibility remains, however, that further metabolism of 1α,25-dihydroxyvitamin D is required to elicit any or all of these responses.

2. Background Art

References to various of vitamin D derivatives are extant in the patent and other literature. See, for example, U.S. Pat. Nos.: 3,565,924 directed to 25-hydroxycholecalciferol; 3,697,559 directed to 1,25-dihydroxycholecalciferol; 3,741,996 directed to 1α-hydroxycholecalciferol; 3,907,843 directed to 1α-hydroxyergocalciferol; 3,715,374 directed to 24,25-dihydroxycholecalciferol; 3,739,001 directed to 25,26-dihydroxycholecalciferol; 3,786,062 directed to 22-dehydro-25-hydroxycholecalciferol; 3,847,955 directed to 1,24,25 trihydroxycholecalciferol; 3,906,014 directed to 3-deoxy-1α-hydroxycholecalciferol.

DISCLOSURE OF INVENTION

A new derivative of vitamin D has now been found which displays vitamin D-like activity and which, it is believed, may be a metabolically active form of the vitamin responsible for some of the biological responses mentioned above. This derivative has been identified as 25-hydroxycholecalciferol 26,23-lactone (or, 23,25-dihydroxy-26-carboxy-vitamin $D_3$-γ-lactone). The formation of this compound in high yields from vitamin $D_3$ are consistent with the belief that it is perhaps a metabolically active form of the vitamin responsible for some of the biological responses which vitamin D elicits.

BEST MODE FOR CARRYING OUT THE INVENTION

The isolation and characterization of the vitamin D derivative (metabolite) of this invention was carried out utilizing in one instance plasma of chicks which had received normal levels of vitamin $D_3$ in their diet and in the second instance plasma from chicks which had been given large doses of vitamin $D_3$. The respective isolation and identification procedures followed are set forth in the Examples below.

EXAMPLE 1

Isolation and characterization of metabolite from plasma of chicks raised on maintenance levels of vitamin $D_3$ Twenty-four liters of chick blood was obtained from 8-week old "fryers" (A-G Coop, Arcadia, Wisconsin) that had received maintenance levels of vitamin $D_3$ in their diet (@ 1000 IU of vitamin $D_3$ per pound of feed). Upon collection, 10% by volume of 0.1 M sodium oxalate, pH 7.0, was added to prevent clotting. The blood was separated in a De Laval blood separator yielding 16 liters of plasma.

The plasma was extracted in 1 liter batches using the following procedure:

Plasma was heated with stirring at 70° C. for 1 hr, then centrifuged for 1 hr at 13,000 rpm in a Beckman J-21C centrifuge equipped with a JA-14 rotor (Beckman Instruments, Inc.). The recovered pellet was suspended in 400 ml of distilled water and extracted for 1 hr at 4° C. with 800 ml of methanol and 400 ml of chloroform. Four-hundred ml of chloroform was then added, the chloroform layer removed and the aqueous phase washed with an additional 400 ml of chloroform. From the combined chloroform phases solvent was removed by evaporation.

The entire chloroform extract was partitioned in 500 ml of hexane and 500 ml of 10% water in methanol with shaking for 1 hr. Five-hundred ml of chloroform was then added to the water-methanol phase. The chloroform phase was collected and aqueous phase washed with 500 ml chloroform twice. The combined chloroform phases were concentrated and used for subsequent chromatography.

The concentrated chloroform extract was chromatographed in four batches on a 3×30 cm Sephadex LH-20 (a hydroxypropyl ether derivative of a polydextran marketed by Pharmacia Fine Chemicals, Inc., Piscataway, N.J.) column eluted with 9:1:1 hexane:chloroform:methanol. Column fractions were assayed using the competitive protein binding radioassay method of Haddad et al. (Arch. Biochem. Biophys. 182, 390, 1977) and the binding peak eluting in the 618 to 807 ml region was pooled and concentrated.

Combined fractions from this peak were further chromatographed in three batches on a 2×55 cm Sephadex LH-20 column eluted with 70:30 chloroform:hexane. Fractions were assayed as above and the binding fractions eluting in the 24,25-dihydroxyvitamin $D_3$ (24,25-$(OH)_2D_3$) region (252 to 318 ml) were pooled and concentrated.

This pooled fraction was further chromatographed in three batches on a 1×58 cm Sephadex LH-20 column eluted with 9:1:1 hexane:chloroform:methanol. Fractions were assayed as above and those eluting in the 25,26-dihydroxyvitamin $D_3$ (25,26-$(OH)_2D_3$) region (133 to 162 ml) were pooled and concentrated.

High pressure liquid chromatography (HPLC) was performed on this component using a Waters Model ALP/6PC 204 instrument (Waters Associates, Milford, Mass.) equipped with a model 440 absorbance detector monitoring at 254 mm and a 0.46×25 cm Partisil ODS (octadecyl silane boned to silica, available from Whatman, Inc., Clifton, New Jersey) column eluted with 25% water in methanol. Fractions were assayed and the binding peak, which matched the UV (254 nm) absorbing peak, eluting from 25.5 to 28.5 ml was pooled. This component was subjected to further HPLC on a 0.46×25 cm microparticulate silica gel column (Waters Associates) eluted with 8% isopropanol in hexane. Fractions were assayed as above and the sole binding component (and major UV (254 nm) absorbing peak) eluting from 14.5 to 16.5 ml was pooled. This fraction was rechromatographed using the same system and the sole UV absorbing peak was collected.

UV spectra of the compound collected in ethanol yielded $\lambda_{max}=264$ nm, $\lambda_{min}=229$ nm, $OD_{264}/OD_{229}=1.40$. A mass of 8 μg was calculated assuming an extinction coefficient of 18,600 and molecular weight of 428.

Mass spectrometry of the compound yielded the following ions and intensities: m/e 428, 27.6%, $M^+$; m/e 410, 4.1%, $M^+$-$H_2O$; m/e 395, 12%, $M^+$-$H_2O$-$CH_3$; m/e 271, 4.5%, $M^+$-side chain; m/e 253, 9.3%, $M^+$-side chain-$H_2O$; m/e 136, 100%, A ring+C-6, C-7 and C-19; m/e 118, 94%, A ring and C-6, C-7, C-19-$H_2O$.

High resolution mass spectrometry on the molecular ion of the compound yielded a weight of 428.2901 for a formula of $C_{27}H_{40}O_4$ (calculated weight=428.2926).

The trimethylsilyl derivative of the compound was prepared from 1 μg using 30 λ pyridine and 25 λ N,O-bis(trimethylsilyl) trifluoroacetamide at 55° C. for 40 minutes. The reaction mixture was subjected directly to mass spectrometry and yielded: m/e 572, 20%, $M^+$; m/e 482, 15%, $M^+$-HOTMS; m/e 467, 10%, $M^+$-HOTMS-$CH_3$; m/e 208, 34%, A-ring fragment; m/e 118, 100%, A ring fragment-HOTMS.

EXAMPLE 2
Isolation of metabolite from plasma of chicks given large doses of vitamin $D_3$ Seventy-one, ten-week old male chicks were dosed intramuscularly with $10^5$ IU vitamin $D_3$ in 50 λ (λ=0.001 cc) ethanol daily for three days. They were then dosed with $10^7$ IU vitamin $D_3$ intramuscularly in four doses in 50 λ of ethanol. Five days after the last dose, the chicks were bled by cardiac puncture using a small amount of heparin to avoid clotting. The blood was immediately centrifuged yielding 1100 ml of plasma.

The plasma was extracted in about 400 ml batches with 800 ml methanol and 400 ml chloroform. After standing 1 hr at 4° C., an additional 400 ml chloroform was added and the chloroform phase collected. The aqueous phase was washed with 400 ml chloroform and combined chloroform phases concentrated by solvent evaporation for chromatography.

The entire concentrated extract was chromatographed on a 3×30 cm Sephadex LH-20 column eluted with 9:1:1 hexane:chloroform:methanol. Fractions were assayed as before and the binding component eluting in the 608 to 931 ml region was pooled and concentrated. This peak was then chromatographed on a 2×55 cm Sephadex LH-20 column eluted with 70:30 chloroform-hexane. Fractions were assayed and the binding component eluting in the 240 to 258 ml region was pooled and concentrated. This fraction was subjected to HPLC on a 0.46×25 cm Partisil ODS column eluted with 25% water in methanol. The major UV (254 nm) absorbing peak was collected (18–22.5 ml) and rechromatographed using the same system. The UV (254 nm) absorbing substance was further purified by HPLC on a 0.46×25 cm microparticulate silica gel column eluted with 8% isopropanol in hexane. The UV (254 nm) absorbing compound eluting from 15–17 ml was collected and repurified on the same system.

UV spectra of this and similarly prepared samples gave $\lambda_{max}=264$ nm, $\lambda_{min}=228$ nm, $OD_{264}/OD_{228}=1.51$. A total mass of 56 μg was obtained as calculated from assuming $\epsilon=18,600$.

High resolution mass spectrometry on this compound yielded: m/e 428, 27.6%, $M^+$($C_{27}H_{40}O_4$); m/e 410, 4.1%, $M^+$-$H_2O$; m/e 395, 12%, $M^+$-$H_2O$-$CH_3$; m/e 271, 4.5% $M^+$-side chain; m/e 253, 9.3%, $M^+$-side chain-$H_2O$; m/e 136, 100%, A ring+; m/e 118, 94%, A ring-$H_2O$.

Mass spectra of the TMS derivative of the compound (prepared as described above) yielded: m/e 572, 20%, $M^+$; m/e 482, 15%, $M^+$-HOTMS; m/e 467, 10%, $M^+$-HOTMS-$CH_3$; m/e 208, 34%, A ring+; m/e 118, 100%, A ring+-HOTMS.

The UV spectra and mass spectra of the isolated compound as well as the mass spectra of the TMS (trimethylsilyl) derivative were identical to those for the compound obtained from the plasma of chicks reared on maintenance levels of vitamin $D_3$, indicating that the identical compound was recovered in each isolation.

The compound was repurified by HPLC on silica gel as described above and the proton NMR was taken in $CDCl_3$ solution on a 270 megahertz instrument. The spectrum obtained was identical to that of 25-hydroxyvitamin $D_3$ (25-OH-$D_3$) except for the following resonances: δ4.46, m, 1H, C-23-H; δ1.56, s, 3H, C-27-$H_3$; δ1.09, d,j=6.3 Hz, sH, C-21-$H_3$; δ0.63, s, 3H, C-18-$H_3$.

A Fourier transform infrared spectrum (FT-IR) was taken of this compound on a Nicolet 7199 FT-IR instrument (Nicolet Instrument Corp., Madison, Wis.). The spectra obtained was very similar to a vitamin $D_3$ spectrum except for an intense absorbance at 1787 cm$^{-1}$, indicative of a γ-lactone.

The methyl lactol product of the TMS derivative of the compound was prepared by mixing 1 μg of $(TMS)_2$-compound with 25 λ of 0.01 M MeLi in diethyl ether at room temperature for 1 hr. The reaction mixture was quenched with 50 λ water and extracted twice with 200 λ methylene chloride. The reaction mixture was purified by HPLC on a 0.4×25 cm silica gel column eluted with 5% ethylacetate in hexane. The UV (254 nm) absorbing compound (elutes from 30 to 42 ml) was collected and subjected to mass spectrometry. The following diagnostic ions of the methyl lactol were obtained: m/e 588, 4.4%, $M^+$; m/e 570, 7.3%, $M^+$-$H_2O$; m/e 528, 1.5%, $M^+$-HOAc; m/e 498, 2%, $M^+$-HOTMS; m/e 208, 33%, A ring+; m/e 118, 100%, A ring+-HOTMS.

The methyl lactol was silylated as above and the mass spectra yielded the following diagnostic ions: m/e 660, 12.7%, $M^+$; m/e 645, 1.8%, $M^+$-$CH_3$; m/e 570, 4%, $M^+$-HOTMS; m/e 555, 2%, $M^+$-HOTMS-$CH_3$; m/e 528, 10%, $M^+$-AcOTMS; m/e 208, 54%, A ring+; m/e 118, 100%, A ring+-HOTMS.

The only structure consistent with all the above spectral data, i.e., the UV, IR, NMR and mass spectrometry, is the 25-hydroxy-cholecalciferol-26,23-lactone, or 3β,25-dihydroxy-9,10-seco-5,7, 10(19)-cholestatrieno-26,23-lactone.

The compound of this invention can be characterized by the following formula:

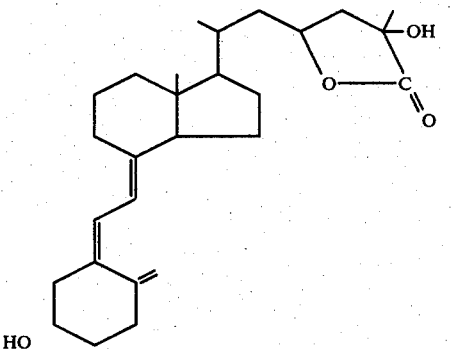

BIOLOGICAL ACTIVITY

Male rats (Holtzman Co., Madison, Wis.) were housed invidually in hanging wire cages and given food and water ad libitum. They were fed for three weeks on the low calcium purified diet described by Suda et al (J. Nutr. 100, 1049 to 1050 (1970)). The rats in groups of seven each, were dosed intrajugularly with 50 λ ethanol(control) or 50 λ of ethanol containing 300 ng of 25-hydroxycholecalciferol-26,23-lactone.

At 12 hours after dosing the rats were decapitated and the blood was collected. It was immediately centrifuged, and 0.1 ml of serum was diluted with 1.9 ml of 0.1% lanthanum chloride solution. Serum calcium concentrations were determined using an atomic absorption spectrometer Model 403 (Perkin-Elmer, Norwalk, Conn.). Results obtained are tabulated below.

| | Serum Calcium (mg/100ml) | | |
|---|---|---|---|
| Rat No. | Control | Rat No. | Lactone |
| 1 | 4.52 | 1 | 4.33 |
| 2 | 4.26 | 2 | 4.48 |
| 3 | 3.94 | 3 | 4.67 |
| 4 | 4.20 | 4 | 4.84 |
| 5 | 4.39 | 5 | 4.72 |
| 6 | 4.70 | 6 | 5.01 |
| 7 | 4.50 | 7 | 4.63 |
| | Avg. ± S.D. | | Avg. ± S.D. |
| | 4.36 ± 0.25 | | 4.67 ± 0.22 |

The lactone-dosed rats' calcium levels were significantly different from the controls with $P<0.05$ establishing that 25-hydroxycholecalciferol-26,23-lactone has vitamin D-like activity in the mobilization of calcium from bone.

I claim:

1. 25-hydroxycholecalciferol-26,23-lactone in substantially pure form.

* * * * *